United States Patent [19]
Allen, Jr. et al.

[11] Patent Number: 5,433,946
[45] Date of Patent: Jul. 18, 1995

[54] SYNTHESIS AND UTILIZATION OF THERAPEUTIC AGENTS FOR THE TREATMENT OF LYSOSOMAL STORAGE DISEASES

[75] Inventors: Howard J. Allen, Jr., Tonawanda; Richard A. DiCioccio, Getzville, both of N.Y.

[73] Assignee: Health Research Inc., Buffalo, N.Y.

[21] Appl. No.: 181,887

[22] Filed: Jan. 14, 1994

Related U.S. Application Data

[63] Continuation of Ser. No. 775,733, Oct. 11, 1991, abandoned.

[51] Int. Cl.$^6$ .............................................. A61K 38/47
[52] U.S. Cl. ................................. 424/94.3; 424/94.6; 424/94.61; 435/195; 435/200
[58] Field of Search ................... 424/94.3, 94.6, 94.61; 435/195, 200

[56] References Cited

U.S. PATENT DOCUMENTS 4,749,570  6/1988  Poznansky ......................... 424/94.3

OTHER PUBLICATIONS

Allen et al., (Oct. 15, 1990), "Metabolic Correction of Fucosidosis Lymphoid Cells by Galaptin-α-L-Fucosidase Conjugates", Biochemical and Biophysical Resource Communications, (172), pp. 335–340.
Poznansky et al., (1989), "Enzyme Replacement Therapy in Fibroblasts from a patient with Cholesteryl Ester Storage Disease", FASEB (3), pp. 152–156.
Ahmed et al., (1990), "Human Splenic Galaptin: Carbohydrate–Binding Specificity and Characterization of the Combining Site", Biochemistry, 29, pp. 5315–5319.
Barton et al., (1990), "Therapeutic Response to intravenous infusions of glycocerebrosides in a patient with Gaucher disease", Proc. Natl. Acad. Sci., 87, pp. 1913–1916.
Hasholt et al., 1988, Clinical Genetics, 33, pp. 360–371.
Fukuda, M., (1985), Biochimica et Biophysica Acta, 780, pp. 119–150.

*Primary Examiner*—Marian C. Knode
*Assistant Examiner*—Jean C. Witz
*Attorney, Agent, or Firm*—Hodgson, Russ, Andrews, Woods & Goodyear

[57] ABSTRACT

The present invention provides compositions wherein endogenous lectins are used as transport vehicles for facilitating the cell-specific binding and cellular uptake of therapeutic agents useful in the treatment of lysosomal storage diseases. In accordance with one embodiment, lectin-glycosidase conjugates are provided for enzyme replacement therapy of cells containing deficient enzyme activity. In accordance with another embodiment, compositions comprising lectin-nucleic acid constructs are provided for gene therapy of cells containing deficient enzyme activity. A third embodiment of the present invention relates to lectin-oligonucleotide compositions provided for antisense therapy to modulate production of mutant and defective lysosomal enzymes.

2 Claims, No Drawings

SYNTHESIS AND UTILIZATION OF THERAPEUTIC AGENTS FOR THE TREATMENT OF LYSOSOMAL STORAGE DISEASES

This invention was made with government support under grants CA42584 and DK32161 awarded by the National Institutes of Health. The government has certain rights in the invention.

This is a continuation of application Ser. No. 07/775,733 filed on Oct. 11, 1991, now abandoned.

FIELD OF THE INVENTION

The present invention relates generally to the treatment of lysosomal storage disease and, more particularly, to the synthesis and utilization of compositions to be delivered to and uptaken by cells deficient in lysosomal enzyme activity.

BACKGROUND OF THE INVENTION

Lysosomal storage diseases are a group of over thirty individual lethal inborn errors of metabolism (Glew et al., 1985, Laboratory Investigation 53:250-269). The diseases are typically caused by either deficient synthesis, or synthesis in a functionally-defective form, of any of various intracellular enzymes important in the metabolic or catabolic functions of the cell. Within the lysosomes of certain cells of people suffering from lysosomal storage diseases, are abnormally accumulated substances such as lipids and/or polysaccharides. The accumulation of these substances intracellularly can cause cell and organ dysfunction resulting in a range of clinical manifestations and may ultimately result in premature death.

Deficient enzyme activity, whether due to a defect in the synthesis of the enzyme or synthesis in a functionally-defective form, may be compensated for by the presence in sufficient quantities of the active enzyme. Enzyme replacement therapy for the purpose of metabolically correcting lysosomal storage disease has been attempted in both human clinical trials and animal model studies (Tager et al., pp.343-359 in *Enzyme Therapy in Genetic Diseases*, Alan R. Liss, New York, 1980; Grabowski et al., pp.167-208 in *Enzymes as Drugs*, John Wiley & Sons, New York, 1981; Brady, R. O., pp. 181-193 in *Genetics of Neurological and Psychiatric Disorders*, Raven Press, New York, 1983).

A major problem encountered in both the human clinical trials and the animal model studies was the virtual exclusive clearance of the administered enzyme by the liver. Current modes of enzyme replacement therapy, involving the injection of an active form of the enzyme into the body of an individual suffering from a lysosomal storage disease, have several problems in addition to rapid clearance from the body. Repeated injections of enzyme derived from a heterologous species may lead to the subsequent development of a hypersensitivity reaction by the individual. Development of such an immune response by the individual may not only undesirably enhance the clearance of the enzyme, but also may result in a clinically manifested, life-threatening reaction. Another problem is the potential for bio-inactivation of the administered enzyme by proteolytic enzymes found circulating in the bloodstream. To compensate for rapid clearance from the body, or for bio-inactivation, and because the administered enzyme is not specifically targeted to the cells containing deficient enzyme activity, the active enzyme has been administered in quantities much greater than the body needs. This in turn may undesirably increase the chances of developing a hypersensitivity reaction.

One strategy for improved delivery of active enzymes has involved exploitation of receptor-mediated uptake systems of cells (Poznansky, M. J., 1983, Pharmac. Ther. 21, 53-76). Receptor-mediated uptake (adsorptive endocytosis) refers to the cellular uptake of macromolecules for which there are binding sites accessable on the plasma membrane or outer surface of a cell. Recent attempts of enzyme replacement therapy for Gaucher's disease, a lysosomal storage disease, utilizing receptor-mediated uptake include modifying the carbohydrate moiety of the enzyme glucocerebrosidase by deglycosylation to produce an enzyme preparation with potential for specificity in receptor binding (Barton et al., 1990, Proc. Natl. Acad. Sci. USA 87:1913-1916). While administration of the altered enzyme appeared to result in some clinical improvement, there is a need for a composition which would facilitated more efficient uptake of the active enzyme than accomplished by free enzyme alone, in efforts to improve enzyme replacement thereapy.

Lectins, proteins having specific carbohydrate-binding activity, have been suggested as transport vehicles potentially useful for the targeted delivery of therapeutic agents (Shier, W. T. pp. 43-70, in *Drug Carriers in Biology and Medicine*, Academic Press, London, 1979. U.S. Pat. No. 4,749,570 discloses the approach of targeting delivery of enzymes by the use of a targeting agent-enzyme-albumin conjugate. The targeting agents disclosed are hormones, lectins, and cell-specific antibodies. The purpose of the albumin is to mask antigenicity of the conjugate. In U.S. Pat. No. 4,749,570, the conjugates were demonstrated to bind to their target cells, and in one instance to be internalized. It was not disclosed if all targeting agents used in U.S. Pat. No. 4,749,570 facilitated the uptake of the conjugate. In addition, where internalization was disclosed, it was not apparent that active enzyme reached and acted upon any accumulated substrate. Internalization of a complex such as a conjugate is just one step in the process of cellular enzyme replacement thereapy. Other crucial steps include avoiding interacellular digestion before enzyme action; reaching the appropriate cellular compartment(s) deficient in enzyme activity; and enzyme activity by the internalized complex on the appropriate endogenous substrate(s). Therefore a need exists for a composition that may facilitate the uptake of active enzyme by a cell deficient in enzyme activity, where the active enzyme reaches and acts on accumulated substrate, wherein the composition may not require a masking agent.

Another approach to treatment of genetic diseases is gene therapy. In this approach, genes or nucleic acids are introduced in attempts to replace poor or mutant gene expression. Standard gene therapy involves either injection of genes encoding a therapeutic protein; or removing cells from an affected individual, engineering the cells with new genetic material, and replacing the cells in the body. Problems encountered when injecting genes as a therapeutic treatment include degradation of the nucleic acids before they reach the target cells, and inefficient uptake of nucleic acid constructs by target cells. Problems encountered with genetically engineering cells removed from an individual are difficulties in getting nucleic acids into the cells without destruction or contamination of the cells and difficulties of targeting the genetically engineered cells to the regions of the body which may be sites for therapy.

Thus, a composition containing genes encoding a normal or functional enzyme which will serve to replace poor or mutant gene expression and which may overcome the problems of standard gene therapy is desirable for gene therapy of lysosomal storage diseases.

Additionally, there may be certain lysosomal storage diseases in which a mutant form of the lysosomal enzyme is produced which lacks enzymatic function but which may block the activity of newly introduced functional enzyme. Therapy of such diseases may require inactivation of the mutant gene in addition to introduction of functional enzyme. One approach utilizes antisense technology to inactivate the mutant gene. Since only the sense strand of DNA codes for the mutant enzyme, short oligonucleotides of the complementary strand, the antisense strand, may be used to bind to m-RNA or DNA to block their function in the cell thereby modulating mutant enzyme production. Thus, a composition which can deliver and facilitate uptake of oligonucleotides may be useful in antisense therapy of lysosomal storage diseases.

OBJECTS AND SUMMARY OF THE INVENTION

It is therefore an object of the present invention to provide an improved delivery of a therapeutic agent intracellularly for the treatment of lysosomal storage diseases.

Another object of the present invention is to prevent immune responses directed to the therapeutic agent during this delivery, without a masking agent being required.

Another object of the present invention is to provide a composition useful in gene therapy of lysosomal storage disease, which will function to compensate for cellular enzyme deficiency.

Another object of the present invention is to provide a composition useful in antisense therapy of lysosomal storage disease which will function to modulate mutant enzyme production.

In accordance with the present invention a composition is provided for therapeutically treating an individual suffering from a lysosomal storage disease. The therapeutic agent comprises a lectin of endogenous origin coupled to an active form of an endogenous lysosomal enzyme of the type which is deficient due to the lysosomal storage disease, so that improved uptake may be achieved and an immune response may be precluded without the use of a masking agent. Upon administration to the individual, and subsequent targeted delivery and cellular uptake of the therapeutic agent by cells containing the enzyme deficiency, the active form of the enzyme compensates for the cellular enzyme deficiency. In another embodiment of the invention, the composition comprises a lectin of endogenous origin and a nucleic acid construct encoding a lysosomal enzyme of a type which is deficient due to the lysosomal storage disease, wherein the enzyme, in active form, compensates for the cellular enzyme deficiency. Another embodiment of the present invention relates to the administration of a therapeutic agent comprising a lectin of endogenous origin and antisense oligonucleotides to modulate mutant enzyme production to enhance the activity of newly introduced functional enzyme.

In accordance with the present invention, endogenous substances are provided to be biocompatible, capable of providing enzymatic activity, and substantially non-immunogenic and non-toxic.

DETAILED DESCRIPTION OF THE PREFERRED EMBODIMENTS

Lectin-glycosidase conjugates have been synthesized and characterized in accordance with the present invention which have potential for therapeutic application in the treatment of lysosomal storage diseases, The lysosomal enzymes which can be used in synthesizing the conjugates include the enzymes listed in Table 1, The present invention is meant to be applicable to the treatement of other lysosomal storage diseases resulting from other enzyme deficiencies which are not listed in Table 1.

TABLE 1

| LYSOSOMAL STORAGE DISEASES | |
| --- | --- |
| Primary enzyme deficiency | Disease name |
| 1-Aspartamido-β-N-acetyl-glucosamine amidohydrolase | Aspartyl-glycosaminuria |
| α-L-Fucosidase | Fucosidosis |
| α-Mannosidase | Mannosidosis |
| Neuraminidase | Sialidosis |
| β-Galactosidase | Gangliosidosis |
| β-Hexosaminidase | Tay-Sach's |
| α-Galactosidase A | Fabry's |
| β-Hexosaminidase A and B | Sandhoff's |
| β-Glucosidase | Gaucher's |
| Sphingomyelinase | Niemann-Pick |
| Arylsulfatase A | Metachromatic leukodystrophy |
| β-galactosidase | Krabbe's |
| α-L-Iduronidase | Mucopolysaccharidosis I (MPS) |
| Iduronate-2-sulfatase | MPS II |
| Heparan-N-sulfatase | MPS III |
| N-acetyl-α-D-glucosaminidase | MPS III |
| AcetylCoA: α-glucosaminide N-acetyltransferase | MPS III |
| N-Acetyl-α-D-glucosamine-6-sulfatase | MPS III |
| N-Acetyl-galactosamine-6-sulfatase; galactose-6-sulfate sulfatase | MPS IV |
| β-Galactosidase | MPS IV |
| Arylsulfatase B | MPS VI |
| β-Glucuronidase | MPS VII |

In order to provide an improved transport of active enzymes into a cell for treatement of such diseases, in accordance with the present invention a lectin is conjugated to the enzyme. In a general comparison between lectins and antibodies, lectins have several favorable features including the ability to carry agents into the interior of the cells such as through the process of endocytosis (Shier, W. T., p. 66, in *Drug Carriers in Biology and medicine,* Academic Press, London. In order to avoid problems of cytotoxicity and to preclude the development of a hypersensitivity response, the lectin and the enzyme are endogenous. By the term "endogenous" is meant, for the purpose of the specification and the claims, a substance which is isolated from or specific to the species being treated. As understood in the art, the term "lectin" refers to a substance which does not encompass antibodies.

The endogenous lectin exemplified in the present invention is galaptin, a galactoside-binding lectin which can be found in humans as well as in other vertebrate species. Cells having deficient enzymatic activity in lysosomal storage diseases include leukocytes. Therefore, galaptin is a preferable endogenous lectin because it binds to cell-surface receptors, such as lactosaminoglycans, on leukocytes such as lymphoid cells, and possibly other leukocytes. Other suitable endogenous lectins include core-specific lectin and IgE-binding protein.

The present invention will become more apparent to one skilled in the art with reference to the following examples.

EXAMPLE I

Galaptin-α-L-fucosidase Conjugate

Fucosidosis is a lysosomal storage disease characterized by accumulation of fucoglycoconjugates due to an inherited deficiency of α-L-fucosidase activity (Van Hoof, F. and Hers, H. G., 1968, Lancet 1:1198). α-L-Fucosidase is an acid hydrolase that catalyzes the removal of L-fucose from the non-reducing end of simple or complex carbohydrates. It has been shown that fucosidosis lymphoid cells lack a mechanism for significant uptake of the enzyme from culture medium. Lectin-glycosidase conjugates, comprising galaptin and α-L-fucosidase, were prepared to be administered to α-L-fucosidase deficient, Epstein-Barr virus (EBV)-immortalized lymphoid cells from an individual with fucosidosis.

1. Preparation of lectin-glycosidase conjugates

Both the galaptin and α-L-fucosidase used were of human origin. Galaptin was purified from human spleen according to the method of Sharma et al. (Biochemistry 29: 5309–5314, 1990), which article is hereby incorporated by reference. α-L-fucosidase was purified from human omentum according to the method of DiCioccio et al. (J. Biol. Chem. 257:714–718), hereby incorporated by reference. Prior to preparation of galaptin-α-L-fucosidase conjugates, galaptin was alkylated with iodoacetamide according to the method of Allen et al. (J. Cell. Biol. 43:43–57, 1990) hereby incorporated by reference. Galaptin was alkylated to eliminate the thiol requirement for maintenance of carbohydrate binding activity of galaptin. To prepare galaptin-α-L-fucosidase conjugates, 120 ul of 1% glutaraldehyde was slowly added to 1.0 mg galaptin and 0.3 mg fucosidase in 1.0 ml of a solution containing 0.2M NaCl, 1.0 mM $PO_4$, 0.1M lactose, 0.1M α-L-fucose, pH 7.3. The solution was stirred for 17 hours at 4° C. Then, 100 ul of 1.0M Tris, pH 7.3, was added and the sample was incubated for 6 hours at 4° C. Albumin (10 mg) was added and the sample was dialyzed against a solution of 0.5M NaCl, 10.0 mM Tris, pH 7.3. The lectin-enzyme conjugate was then re-purified by affinity chromatography on lactose-Sepharose according to the procedure of Sharma et al. (Biochemistry 29:5309–5314, 1990). The lactose eluate, containing the galaptin-α-L-fucosidase conjugate, was adjusted by the addition of 1.0 mg albumin/ml and then concentrated by centrifugal filtration and stored at 4° C. If storage at −20° C. is desired, glycerol may be added, to a final concentration of 50%, to the product. Carbohydrate binding activity of the conjugate was checked by hemagglutination assay according to the method of Allen et al.(Arch. Biochem. Biophys. 256:523–533, 1987). α-L-fucosidase activity was assayed with 4-methyl-umbelliferyl-α-L fucoside as substrate according to the method of DeCioccio et al. (Biochem. Genet. 26:401–420).

It is important to point out that in the preparation of the lectin-glycosidase conjugate in accordance with the present invention, the albumin was added to the solution containing the conjugate only for the purpose of a carrier protein which will help prevent thermal denaturation of serving as the conjugate in solution, and prevent adsorption of the conjugate to vessel or dialysis tubing surfaces. For such a purpose, covalent or non-covalent interaction between the conjugate and the albumin is not required. Other proteins may be substituted for this purpose.

It is believed that by preparing the galaptin conjugates under the conditions described above, the macromolecular complex of the conjugates may contain galaptin in polymeric form which may further facilitate targeted delivery to and endocytosis by cells.

2. Lymphoid cells used as the target for lectin-glycosidase conjugates

B-lymphoid cell lines used to assay for targeted delivery of the lectin-glycosidase conjugates, as well as for cellular uptake studies, were cell line B-142 which was derived from a healthy individual, and cell line JT which was derived from an individual with fucosidosis. The methods used to establish the cell lines from peripheral blood, detailed background information about the cell lines, and routine culture conditions for cell maintenance have been described by DiCioccio et al. (Biochem. Genet. 26:401–420, 1988) and Willems et al. (Am. J. Hum. Genet. 43:756–763, 1988) which articles are hereby incorporated by reference.

3. Demonstration of the specificity of cell binding of the lectin-glycosidase conjugate The specificity of cell binding of galaptin-α-L-fucosidase conjugates and of purified α-L-fucosidase to lymphoid cells derived from an individual with fucosidosis was determined. The JT lymphoid cells for each binding assay were prepared by suspending $10^6$ cells in 0.1 ml of RPMI 1640 medium containing 0.5% BSA. The conjugate or purified enzyme was tested for cell binding by adding to it the JT cells, and then incubating the mixture at 4° C. for 90 minutes. Binding was carried out at 4° C. to minimize turnover and/or recycling of putative cell surface receptors during the binding interval. The cells were harvested by centrifugation at 250×g at 4° C. for 10 minutes. The media was removed and saved. The cells were then washed with PBS containing 0.5% BSA and cell extracts were made by treatment of the cells with 25 ul of 1% Triton X-100. The cell extract and medium from each experiment were assayed for α-L-fucosidase activity. The substrate for the enzyme activity assay was 4-methyl-umbelliferyl-α-L fucoside. One unit of enzyme activity is defined as 1 nanomole of substrate hydrolyzed per hour. In this system, binding of the conjugate to the cells is measured by assaying L-fucosidase activity. To further define the specificity of binding, in some assays lactose was added to the cells in addition to the conjugate to test for the ability of lactose to inhibit the binding reaction.

The results of the binding assay are in Table 2.

TABLE 2

| Binding of Galaptin-α-L-Fucosidase Conjugate to Fucosidosis Lymphoid Cells | | | |
|---|---|---|---|
| | Fucosidase Activity (Units) | | |
| Composition tested | Cells | Medium | Total |
| Experiment 1 | | | |
| galaptin-α-L-fucosidase (4 units) | 0.416 | 3.560 | 3.976 |
| galaptin-α-L-fucosidase (4u) + 50 mM lactose | 0.012 | 4.240 | 4.252 |
| α-L-fucosidase (4u) | 0.005 | 4.040 | 4.045 |
| α-L-fucosidase (4u) + 50 mM lactose | 0.010 | 4.140 | 4.150 |
| 50 mM lactose | 0 | 0 | 0 |
| No addition to cells | 0 | 0 | 0 |
| Experiment 2 | | | |
| galaptin-α-L-fucosidase (4u) | 0.320 | 2.880 | 3.200 |

TABLE 2-continued

Binding of Galaptin-α-L-Fucosidase Conjugate
to Fucosidosis Lymphoid Cells

| Composition tested | Fucosidase Activity (Units) | | |
|---|---|---|---|
| | Cells | Medium | Total |
| galaptin-α-L-fucsidase (4u) + 50 mM lactose | 0.007 | 3.680 | 3.687 |
| galaptin-α-L-fucosidase (8u) | 0.567 | 6.080 | 6.647 |
| galaptin-α-L-fucosidase (8u) + 50 mM lactose | 0.020 | 7.680 | 7.700 |
| galaptin-α-L-fucosidase (12u) | 0.733 | 9.760 | 10.493 |
| galaptin-α-L-fucosidase (12u) + 50 mM lactose | 0.027 | 11.580 | 11.547 |
| 50 mM lactose | 0 | 0 | 0 |
| No addition to cells | 0 | 0 | 0 |

In the above separate experiments, cells incubated with conjugate (4 enzyme units) bound 10–10.5% of the total enzyme activity recovered; whereas cells incubated with conjugate in the presence of lactose bound 0.2–0.3%. Thus, binding of conjugate to cells was almost completely inhibited by lactose. Cells incubated with free α-L-fucosidase in the absence or presence of lactose bound 0.1–0.2% of the total enzyme activity recovered. The total enzyme activity recovered is defined as the sum of the enzyme activity recovered from the cell extract and from the medium. Thus, binding of enzyme to cells via galaptin receptors was 50 to 100-fold more efficient than binding of enzyme to endogenous enzyme receptors. As illustrated in Experiment 2 of Table 2, binding of enzyme was dependent upon concentration of the conjugate in the incubation medium since the amount of enzyme bound to cells increased when increasing amounts of conjugate were incubated with the cells.

4. Demonstration of internalization of the conjugate following cell binding

The galaptin-α-L-fucosidase conjugate and the purified α-L-fucosidase were tested for their respective abilities to be internalized by fucosidosis lymphoid cells. JT lymphoid cells, $2 \times 10^6$ cells in 0.2 ml of RPMI 1640 medium containing 0.5% BSA, were incubated with either the lectin-glycosidase conjugate, or α-L-fucosidase, for 90 minutes at 4° C. After this incubation for binding, 0.4 ml of medium containing 0.5% BSA was added to each sample. The cells were then incubated at 37° C. After 0, 1, 2, or 4 hours, the cells were centrifuged at 250×g at 4° C. for 10 minutes. The medium was removed from the cell pellet and saved to be assayed. The cells were washed twice with PBS containing 0.5% BSA and divided into two aliquots of $10^6$ cells each. One aliquot was suspended in 0.1 ml of PBS containing 0.5% BSA with 50 mM lactose and the other aliquot was suspended in PBS without added lactose. Both aliquots were then incubated at 4° C. for 90 minutes to allow displacement of surface-bound conjugate, followed by centrifugation. The supernates were removed and saved for analysis. The cell pellets were washed and extracted with 25 ul of 1% Triton X-100. The cell extracts, media, and the supernates were assayed for α-L-fucosidase activity, the results of which are depicted in Table 3.

TABLE 3

Internalization of Galaptin-α-L-Fucosidase Conjugate By Fucosidosis Lymphoid Cells

| Composition tested | Time interval (hours) | Enzyme Activity* | | | | |
|---|---|---|---|---|---|---|
| | | | + Lactose | | − Lactose | |
| | | Medium | Cells | Supernate | Cells | Supernate |
| Experiment 1: | | | | | | |
| galaptin-α-L-fucosidase conjugate (6u)** | 0 | 5.12 | 0.040 | 0.592 | 0.212 | 0.018 |
| | 1 | 5.92 | 0.088 | 0.464 | 0.194 | 0.096 |
| | 2 | 6.56 | 0.128 | 0.448 | 0.180 | 0.112 |
| | 4 | 5.12 | 0.212 | 0.320 | 0.236 | 0.094 |
| Experiment 2: | | | | | | |
| galaptin-α-L-fucosidase conjugate (18u) | 0 | 17.28 | 0.090 | 0.550 | 0.385 | 0.180 |
| | 4 | 14.88 | 0.255 | 0.220 | 0.315 | 0.120 |
| α-L-fucosidase (18u) | 0 | 20.92 | 0.010 | 0.005 | 0.020 | 0.005 |
| | 4 | 19.68 | 0.015 | 0.005 | 0.015 | 0.005 |

*nmoles substrate hydrolyzed per hour
**u = unit wherein 1 unit of enzyme is the amount which hydrolyzes 1 nmole of substrate per hour.

5. Demonstration of enzyme activity by the internalized conjugate on the accumulated substrate within fucosidosis lymphoid cells To determine if galaptin-α-L-fucosidase conjugate could reduce the accumulation of Fuc-GlcNAc-Asp in fucosidosis lymphoid cells, the cells were metabolically labeled with [$^3$H] L-fucose followed by incubation with conjugate, and assayed for content of [$^3$H] Fuc-GlcNAc-Asn. Fuc-GlcNAc-Asn was isolated from lymphoid cells according to the method of Morton et al. (Cancer Res. 42:3022–3027, 1982). Lymphold cells ($10^6$/ml) in RPMI 1640 medium containing 10% fetal calf serum were incubated with [$^3$H] fucose (10 uCi/ml) for 24 hours at 37° C. Cells were harvested by centrifugation at 250×g for 10 minutes at 4° C. and were washed twice with RPMI 1640 containing 0.5% BSA. Aliquots of $3 \times 10^6$ cells were suspended in 0.3 ml of medium containing 0.5% BSA and the additions as indicated in Table 4. The cells were incubated at 4° C. for 90 minutes to allow binding of conjugate. The cells were then diluted with 2.7 ml of medium containing 0.5% BSA and were incubated at 37° C. for 20 hours to allow for internalization of conjugate. The cells were then harvested for isolation of [$^3$H] Fuc-GlcNAc-Asp with the amount of radioactivity being quantitated in counts per minute (cpm), as illustrated in Table 4.

TABLE 4

Hydrolysis of [$^3$H] Fuc-GlcNAc-Asn in Fucosidosis Lymphoid Cells By Internalized Galaptin - α-L-Fucosidase Conjugate

| | | [$^3$H] Fuc-GlcNAc-Asp | |
|---|---|---|---|
| Cell Type | Addition | CPM | % of control |
| Experiment 1: | | | |
| Fucosidosis (JT) | None (control) | 72840 | 100 |
| Normal (B142) | None | 7740 | 11 |

TABLE 4-continued

Hydrolysis of [³H] Fuc-GlcNAc-Asn in Fucosidosis Lymphoid Cells By Internalized Galaptin - α-L-Fucosidase Conjugate

| Cell Type | Addition | [³H] Fuc-GlcNAc-Asp CPM | % of control |
|---|---|---|---|
| Experiment 2: | | | |
| Fucosidosis (JT) | None | 87380 | 100 |
| (JT) | galaptin-α-L-fucosidase | 3310 | 4 |
| (JT) | galaptin-α-L-fucosidase + 50 mM lactose | 90580 | 104 |
| (JT) | -L-Fucosidase | 85200 | 98 |
| Experiment 3: | | | |
| Fucosidosis (JT) | None | 85970 | 100 |
| (JT) | galaptin-α-L-Fucosidase | 14070 | 16 |
| (JT) | galaptin-α-L-fucosidase + 50 mM lactose | 71570 | 83 |
| (JT) | polygalaptin + α-L-fucosidase | 68230 | 79 |

In each case the galaptin concentration was 191 ug, and the amount of α-L-fucosidase was 432 units.
In Experiment 1, the [³H] Fuc-GlcNAc-Asn was determined after 24 hours of incubation with [³H] fucose.

The data in Table 4 shows that the fucosidosis lymphoid cells accumulated Fuc-GlcNAC-Asn 9-fold more than lymphoid cells derived from a healthy individual. Also shown by the data in Table 4, fucosidosis lymphoid cells treated either with conjugate in the presence of lactose, or with α-L-fucosidase alone, or with an unconjugated mixture of polygalaptin and α-L-fucosidase, were not appreciably different in substrate composition when compared to untreated cells. Therefore, the ability of conjugate to reduce the cellular accumulation of the substrate glycopeptide was dependent upon the binding of covalently linked galaptin-α-L-fucosidase conjugate to a lactose-inhibitable receptor. Also of significance is the data in Table 4 which indicates that treatment of the fucosidosis lymphoid cells with conjugate reduced the accumulation of glycopeptide within these cells to a level similar to that found in lymphoid cells derived from a healthy individual. This finding suggests that galaptin-α-L-fucosidase conjugate may be useful for enzyme replacement therapy of fucosidosis.

EXAMPLE II

Galaptin-Nucleic Acid Construct in Gene Therapy of Lysosomal Storage Disease

In this embodiment of the present invention, galaptin is used as a transport vehicle to deliver and facilitate uptake of a nucleic acid construct which may help to metabolically correct deficient enzyme activity in the affected cells in lysosomal storage diseases. In accordance with the present invention, galaptin of endogenous origin is linked to a nucleic acid construct which contains one or more copies of a gene encoding a normal or functional enzyme which will serve to replace poor or mutant gene expression encountered in a lysosomal storage disease. This newly introduced nucleic acid construct may be engineered so that the gene encoding the functional enzyme may integrate into the target cells' DNA or exist in the cytoplasmic compartment of the cells. The galaptin-nucleic acid construct may overcome the problems of standard gene therapy. The galaptin will serve in target-mediated delivery of the nucleic acid construct thereby reducing the time in the circulatory system and the exposure to endogenous nucleases. Additionally, the use of galaptin as a transport vehicle has been shown, in Example I, to mediate uptake of the therapeutic agent by the target cells. Since the galaptin-nucleic acid composition may be administered in-vivo, by injection into the body of an affected individual, this compound overcomes the problems associated with removing and genetically engineering cells.

The construction of a composition comprising an endogenous lectin and a nucleic acid construct may require the use of a chemical linking agent. For example, purified galaptin may be mixed with poly-lysine, or another suitable compound, resulting in galaptin chemically linked to poly-lysine. This galaptin-poly-lysine compound may then be purified by standard chromatographic techniques. The human gene for α-L-fucosidase, which has been isolated (Occhiodoro et al., 1989, Biochem. Biophys. Res. Comm. 164:439–445), may be cloned into a vector. The resultant nucleic acid constructs may then be mixed with the galaptin-poly-lysine compound resulting in ionic linkage of the constructs to the poly-lysine of the galaptin-poly-lysine compound. The resultant compound, comprising galaptin-poly-lysine-nucleic acid construct, may be purified utilizing chromatographic techniques prior to use in gene therapy of fucosidosis.

Similar techniques may be used in linking endogenous lectin to oligonucleotides in the formation of a compound which may be useful in antisense therapy of lysosomal storage diseases. For example, a compound may be produced which comprises galaptin-poly-lysine-oligonucleotides wherein the oligonucleotides are short pieces of the antisense strand complementary to a mutant lysosomal enzyme gene.

It is understood that the embodiments of the present invention as described herein are for purposes of illustration only, and not limitation, and any changes or modifications as will become apparent to one skilled in the art from the foregoing description are intended to be included within the scope of the appended claims. For example, other conjugation methods using homo- or heteroactive crosslinkers may be used in producing the compounds of the present invention. It will also be apparent that other lectins and therapeutic proteins may be used to produce therapeutic conjugates. Furthermore, the composition of the conjugates may require a polymer such as polyethylene glycol or cyclodextrin to reduce immunogenicity of the compounds.

We claim:

1. A lectin-enzyme conjugate consisting essentially of human galaptin as a lectin targeting agent, and human α-L-fucosidase as a functional lysosomal enzyme, wherein the galaptin-α-L-fucosidase conjugate is internalized by human fucosidosis lymphoid cell-associated galaptin receptor-mediated endocytosis; accesses cellular lysosomal compartments deficient in α-L-fucosidase activity; and the α-L-fucosidase of the conjugate enzymatically reduces the level of accumulated substrate fucoglycoconjugates within the lysosomal compartments.

2. A method for treating human cells in need of α-L-fucosidase enzyme replacement therapy, said method comprising contacting said cells with a therapeutically effective amount of a lectin-enzyme conjugate consisting essentially of human galaptin as a lectin targeting agent, and human α-L-fucosidase as a functional lysosomal enzyme, wherein the galaptin-α-L-fucosidase conjugate
   (a) is internalized by said treated cells through a cell-associated galaptin receptor-mediated endocytosis;
   (b) accesses cellular lysosomal compartments deficient in α-L-fucosidase activity; and
   (c) the α-L-fucosidase of the conjugate enzymatically reduces the level of accumulated substrate fucoglycoconjugates within the lysosomal compartments of said treated cells.

* * * * *